US012575810B2

(12) United States Patent
Kim et al.

(10) Patent No.: US 12,575,810 B2
(45) Date of Patent: Mar. 17, 2026

(54) DIRECTION DEPENDENT MULTI-MODE ULTRASOUND IMAGING

(71) Applicant: Samsung Medison Co., Ltd., Hongcheon-gun (KR)

(72) Inventors: Mose Kim, Seoul (KR); Yoonchang Lee, Seoul (KR)

(73) Assignee: SAMSUNG MEDISON CO., LTD., Hongcheon-Gun (KR)

( * ) Notice: Subject to any disclaimer, the term of this patent is extended or adjusted under 35 U.S.C. 154(b) by 6 days.

(21) Appl. No.: 18/400,500

(22) Filed: Dec. 29, 2023

(65) Prior Publication Data
US 2025/0072871 A1    Mar. 6, 2025

(30) Foreign Application Priority Data
Sep. 5, 2023    (KR) ........................ 10-2023-0117630

(51) Int. Cl.
*A61B 8/00*    (2006.01)

(52) U.S. Cl.
CPC ............ *A61B 8/5207* (2013.01); *A61B 8/463* (2013.01); *A61B 8/466* (2013.01); *A61B 8/481* (2013.01); *A61B 8/485* (2013.01); *A61B 8/488* (2013.01); *A61B 8/5238* (2013.01)

(58) Field of Classification Search
None
See application file for complete search history.

(56) References Cited

U.S. PATENT DOCUMENTS

| | | | |
|---|---|---|---|
| 6,245,017 B1 * | 6/2001 | Hashimoto | .............. A61B 8/06 |
| | | | 600/447 |
| 9,651,662 B2 | 5/2017 | Kruecker et al. | |
| 9,700,284 B2 | 7/2017 | Kapoor et al. | |

(Continued)

FOREIGN PATENT DOCUMENTS

| | | |
|---|---|---|
| JP | 2015-97634 A | 5/2015 |
| JP | 5773642 B2 | 9/2015 |

OTHER PUBLICATIONS

Doherty et al., "The development of a combined b-mode, ARFI, and spectral Doppler ultrasound imaging system for investigating cardiovascular stiffness and hemodynamics," (Mar. 25, 2011), Proceedings vol. 7968, Medical Imaging 2011: Ultrasonic Imaging, Tomography, and Therapy. (Year: 2011).*

(Continued)

*Primary Examiner* — Keith M Raymond
*Assistant Examiner* — Ashish S. Jasani
(74) *Attorney, Agent, or Firm* — Morgan Lewis & Bockius LLP

(57) ABSTRACT
Provided is an ultrasound imaging apparatus including a display, a memory storing one or more instructions, and a processor configured to execute the one or more instructions stored in the memory, wherein, by executing the one or more instructions, the processor is further configured to generate at least one contrast-enhanced image of an object based on first ultrasonic signals obtained when a probe sweeps the object in a first direction, generate at least one ultrasonic image of the object based on second ultrasonic signals obtained when the probe sweeps the object in a second direction different from the first direction, and control the display to display the at least one contrast-enhanced image and the at least one ultrasonic image.

18 Claims, 16 Drawing Sheets

(56) References Cited

U.S. PATENT DOCUMENTS

| | | | | |
|---|---|---|---|---|
| 11,083,435 | B2 | 8/2021 | Moshavegh et al. | |
| 2003/0055308 | A1* | 3/2003 | Friemel ................... | A61B 8/14 |
| | | | | 600/15 |
| 2005/0113689 | A1 | 5/2005 | Gritzky | |
| 2008/0294045 | A1* | 11/2008 | Ellington ............. | A61B 8/4483 |
| | | | | 600/447 |
| 2011/0160590 | A1* | 6/2011 | Waki ........................ | A61B 8/08 |
| | | | | 600/443 |
| 2013/0165793 | A1* | 6/2013 | Kim ........................ | A61B 8/488 |
| | | | | 600/453 |
| 2015/0141828 | A1 | 5/2015 | Yoshiara et al. | |
| 2018/0035979 | A1 | 2/2018 | Herbst et al. | |
| 2020/0121297 | A1* | 4/2020 | Kim .................... | A61B 8/5246 |

OTHER PUBLICATIONS

Extended European Search Report dated Jun. 7, 2024, issued in corresponding European Patent Application No. 23219702.0.
European Communication dated Oct. 22, 2025 issued in European Patent Application No. 23219702.0.

* cited by examiner

<u>100a</u>

100c

START

GENERATE CONTRAST-ENHANCED IMAGE BASED ON
FIRST ULTRASONIC SIGNALS OBTAINED WHEN PROBE
SWEEPS OBJECT IN FIRST DIRECTION — S310

GENERATE ULTRASONIC IMAGE BASED ON SECOND
ULTRASONIC SIGNALS OBTAINED WHEN PROBE
SWEEPS OBJECT IN SECOND DIRECTION — S320

DISPLAY CONTRAST-ENHANCED IMAGE AND
ULTRASONIC IMAGE — S330

END

1310

DIRECTION DEPENDENT MULTI-MODE ULTRASOUND IMAGING

CROSS-REFERENCE TO RELATED APPLICATION

This application is based on and claims priority under 35 U.S.C. § 119 to Korean Patent Application No. 10-2023-0117630, filed on Sep. 5, 2023, in the Korean Intellectual Property Office, the disclosure of which is incorporated by reference herein in its entirety.

BACKGROUND

1. Field

One or more embodiments of the disclosure relate to an ultrasound imaging apparatus, and more particularly, to an ultrasound imaging apparatus capable of obtaining a contrast-enhanced image and a tissue image of an object and an operating method thereof.

2. Description of the Related Art

Recently, various medical imaging apparatuses for imaging and obtaining information about tissues and organs of the human body have been widely used for the purposes of early diagnosis and treatment of diseases. Such medical imaging apparatuses may include an ultrasound diagnostic apparatus, a computed tomography (CT) apparatus, and a magnetic resonance imaging (MRI) apparatus.

Ultrasound diagnostic apparatuses obtain an image of a part inside an object by irradiating an ultrasonic signal generated from a transducer of a probe to the object and receiving information about an echo signal reflected from the object. In particular, ultrasound diagnostic apparatuses are used for medical purposes, such as observation of an inside part of an object, detection of foreign matters, measurement of injury, etc. As ultrasound diagnostic apparatuses have higher stability than other diagnostic apparatuses using X-ray, are capable of displaying an image in real time, and are free from radiation exposure, ultrasound diagnostic apparatuses are widely used along with other image diagnostic apparatuses.

Lately, contrast-enhanced images obtained by using an ultrasound contrast agent have been widely used for diagnosis of various lesions. Ultrasound contrast agents may be injected into the human body, and the injected ultrasound contrast agent may circulate inside the human body. Microbubbles of the contrast agent may function as a strong reflector for ultrasonic signals. Accordingly, ultrasonic signals reflected from microbubbles are shown as a strong signal in an ultrasonic image, compared to normal tissues.

SUMMARY

Provided are an ultrasound imaging apparatus capable of providing a contrast-enhanced image and a tissue image of an object and an operating method thereof.

Additional aspects will be set forth in part in the description which follows and, in part, will be apparent from the description, or may be learned by practice of the presented embodiments of the disclosure.

In accordance with an aspect of the disclosure, an ultrasound imaging apparatus includes a display, a memory storing one or more instructions, and a processor configured to execute the one or more instructions stored in the memory, wherein, by executing the one or more instructions, the processor is further configured to generate at least one contrast-enhanced image of an object based on first ultrasonic signals obtained when a probe sweeps the object in a first direction, generate at least one ultrasonic image of the object based on second ultrasonic signals obtained when the probe sweeps the object in a second direction different from the first direction, and control the display to display the at least one contrast-enhanced image and the at least one ultrasonic image.

The first ultrasonic signals may include contrast-enhanced signals reflected from a contrast agent, and the second ultrasonic signals may include tissue signals reflected from tissues of the object.

The processor may be further configured to execute the one or more instructions to generate, based on the first ultrasonic signals, contrast-enhanced images corresponding to first cross-sections of the object which do not intersect each other and generate, based on the second ultrasonic signals, ultrasonic images corresponding to second cross-sections of the object which do not intersect each other, wherein the first cross-sections are different from the second cross-sections.

The first cross-sections and the second cross-sections may not intersect each other.

The processor may be further configured to execute the one or more instructions to perform compensation for the first ultrasonic signals by applying a first gain value to the first ultrasonic signals obtained from a first area in which the first cross-sections and the second cross-sections intersect each other and applying a second gain value to the first ultrasonic signals obtained from areas other than the first area, wherein the first gain value is set to be greater than the second gain value.

The processor may be further configured to execute the one or more instructions to generate a three-dimensional (3D) contrast-enhanced image based on the contrast-enhanced images corresponding to the first cross-sections and generate a 3D ultrasonic image based on the ultrasonic images corresponding to the second cross-sections.

The 3D contrast-enhanced image may have a first resolution, and the 3D ultrasonic image may have a second resolution different from the first resolution.

The processor may be further configured to execute the one or more instructions to set the number of the contrast-enhanced images constituting the 3D contrast-enhanced image to be different from the number of the ultrasonic images constituting the 3D ultrasonic image.

The first resolution may be determined based on at least one of the number of the contrast-enhanced images constituting the 3D contrast-enhanced image or the number of scanlines constituting one contrast-enhanced image, and the second resolution may be determined based on at least one of the number of the ultrasonic images constituting the 3D ultrasonic image or the number of scanlines constituting one ultrasonic image.

A volume rate of the 3D contrast-enhanced image and the 3D ultrasonic image may be determined based on the number of the contrast-enhanced images constituting the 3D contrast-enhanced image, the number of scanlines constituting one contrast-enhanced image, the number of the ultrasonic images constituting the 3D ultrasonic image, and the number of scanlines constituting one ultrasonic image.

The at least one ultrasonic image may include at least one of a tissue image, a Doppler image, an elastography image, or a microvascular image.

The processor may be further configured to execute the one or more instructions to generate at least one second ultrasonic image of the object based on third ultrasonic signals obtained when the probe sweeps the object in a third direction different from the first direction and the second direction and control the display to display the at least one second ultrasonic image.

In accordance with another aspect of the disclosure, a method of operating an ultrasound imaging apparatus includes generating at least one contrast-enhanced image of an object based on first ultrasonic signals obtained when a probe sweeps the object in a first direction, generating at least one ultrasonic image of the object based on second ultrasonic signals obtained when the probe sweeps the object in a second direction different from the first direction, and displaying the at least one contrast-enhanced image and the at least one ultrasonic image.

BRIEF DESCRIPTION OF THE DRAWINGS

The present disclosure will become apparent and more readily appreciated from the following description, taken in conjunction with the accompanying drawings wherein like reference numerals denote like structural elements.

The above and other aspects, features, and advantages of certain embodiments of the disclosure will be more apparent from the following description taken in conjunction with the accompanying drawings, in which.

DETAILED DESCRIPTION

Figure 1:
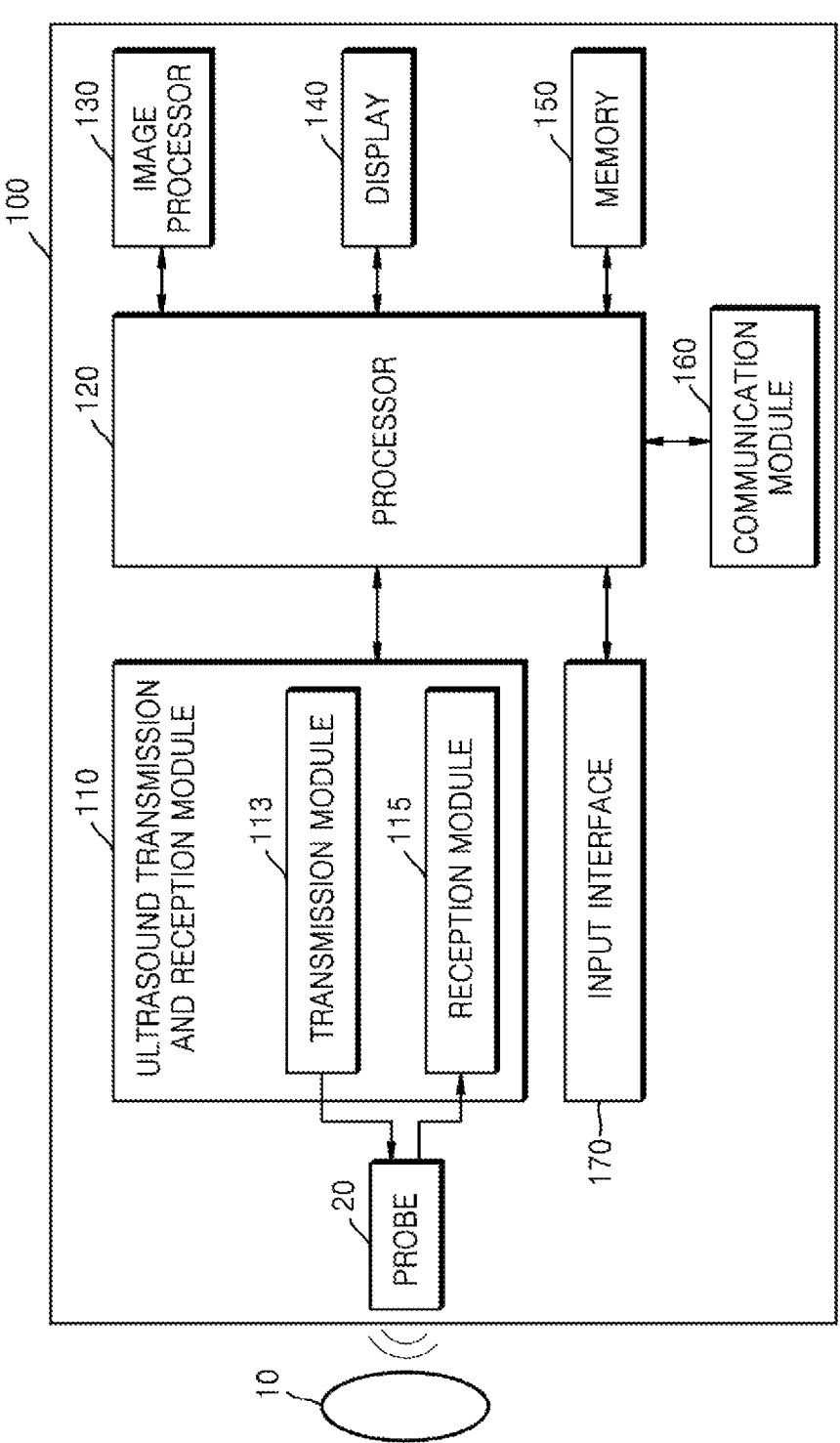
FIG. 1 is a block diagram illustrating components of an ultrasound imaging apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The specification is intended to describe the principle and embodiments of the disclosure such that the scope of rights of the disclosure is clarified, and the disclosure may be carried out by a person skilled in the art. The embodiments of the disclosure may be embodied in many different forms.

Throughout the specification, like reference numerals denote like components. The specification does not necessarily describe all elements of the embodiments, and general features of the field to which the disclosure pertains and redundant description in the embodiments may be omitted. Such terms as "module" or "unit" used throughout the specification may be implemented by a software, a hardware, or a combination thereof, and in some embodiments, a plurality of "modules" or "units" may be implemented by one element or a "module" or "unit" may include a plurality of elements.

Hereinafter, the operational principle and embodiments of the disclosure are described by referring to the attached drawings.

Throughout the specification, the term "image" may include a medical image obtained by a medical imaging apparatus, such as a magnetic resonance imaging (MRI) apparatus, a computed tomography (CT) apparatus, an ultrasound imaging apparatus, an X-ray apparatus, etc.

The term "object" used herein refers to a target of imaging and may include a person, an animal, or parts thereof. For example, an object may include a body part (organ) or phantom.

Throughout the specification, the term "ultrasonic image" refers to an image of an object, which has been processed based on ultrasonic signals transmitted to and then reflected from the object.

Hereinafter, embodiments of the disclosure will be described in detail with reference to the drawings.

FIG. 1 is a block diagram illustrating components of an ultrasound imaging apparatus 100 according to an embodiment. The ultrasound imaging apparatus 100 according to an embodiment may include a probe 20, an ultrasound transmission and reception module 110, a processor 120, an image processor 130, a display 140, a memory 150, a communication module 160, and an input interface 170.

The ultrasound imaging apparatus 100 may be a cart type apparatus or a portable type apparatus. A portable type ultrasound diagnostic apparatus may include a smartphone, a laptop computer, a personal digital assistant (PDA), a tablet PC, etc., which include a probe and an application; however, the disclosure is not limited thereto.

The probe 20 may include a plurality of transducers. The plurality of transducers may transmit an ultrasonic signal to an object 10 according to a transmission signal applied from a transmission module 113. The plurality of transducers may receive an ultrasonic signal reflected from the object 10 and form a reception signal. The probe 20 may be integrated with the ultrasound imaging apparatus 100 or may be implemented as a separate device connected to the ultrasound imaging apparatus 100 in a wired or wireless manner. The ultrasound imaging apparatus 100 may include a single probe 20 or a plurality of probes 20 according to a type of the ultrasound diagnostic apparatus 100.

The probe 20 according to an embodiment may be a two-dimensional (2D) probe. When the probe 20 is a 2D probe, a plurality of transducers included in the probe 20 may be arranged in a 2D manner and form a 2D transducer array.

For example, a 2D transducer array may include, in a second direction, a plurality of sub-arrays including a plurality of transducers arranged in a first direction different from the second direction.

When the probe 20 is a 2D probe, the ultrasound transmission and reception module 110 may include an analog beamformer and a digital beamformer. Or, a 2D probe may include one of an analog beamformer and a digital beamformer or include both according to its type.

The processor 120 may control the transmission module 113 to form a transmission signal to be applied to each of the plurality of transducers by considering positions and a focusing point of the plurality of transducers included in the probe 20.

The processor 120 may convert a reception signal received from the probe 20 from analog to digital and control a reception module 115 to generate ultrasonic data by summing the digital-converted reception signal considering positions and a focusing point of the plurality of transducers.

Alternatively, when the probe 20 is a 2D probe, the processor 120 may calculate a time delay value for digital beam-forming for each of a plurality of sub-arrays included in a 2D transducer array. In addition, the processor 120 may calculate a time delay value for analog beam-forming for each of a plurality of transducers included in any one of the plurality of sub-arrays. The processor 120 may control the analog beamformer and the digital beamformer to form a transmission signal to be applied to each of the plurality of transducers, according to a time delay value for analog beam-forming and time delay values for digital beam-forming. The processor 120 may control the analog beamformer to sum signals received from the plurality of transducers according to a time delay value for analog beam-forming. The processor 120 may control the ultrasound transmission and reception module 110 to convert signals summed by sub-array from analog to digital. The processor 120 may control the digital beamformer to generate ultrasonic data by summing the digital-converted signals according to a time delay value for digital beam-forming.

The image processor 130 may generate an ultrasonic image by using the generated ultrasonic data.

The display 140 may display the generated ultrasonic image and various information processed in the ultrasound imaging apparatus 100. The ultrasound imaging apparatus 100 may include a single display 140 or a plurality of displays 140 according to a type of the ultrasound imaging apparatus 100. The display 140 may include a touch panel or a touch screen.

The processor 120 may control overall operations of the ultrasound imaging apparatus 100 and a signal flow among internal components of the ultrasound imaging apparatus 100. The processor 120 may control various operations or functions of the ultrasound imaging apparatus 100 by executing a program or instructions stored in the memory 150. The processor 120 may control operations of the ultrasound imaging apparatus 100 by receiving a control signal from the input interface 170 or an external device.

The ultrasound imaging apparatus 100 may include the communication module 160 and may be connected to an external device (e.g., a server, a medical device, or a portable device, such as a smartphone, a table PC, a wearable device, etc.) through the communication module 160.

The communication module 160 may include at least one component enabling communication with an external device and include, for example, at least one of a short-range communication module, a wired communication module, or a wireless communication module.

The communication module 160 may receive a control signal and data from an external device and transmit the received control signal to the processor 120 such that the processor 120 controls the ultrasound imaging apparatus 100 according to the received control signal.

Or, the processor 120 may transmit a control signal to an external device through the communication module 160 to control the external signal according to the control signal of the processor 120.

For example, an external signal may process data of the external signal according to a control signal of the processor 120 received from the communication module 160.

A program for controlling the ultrasound imaging apparatus 100 may be installed in an external device, and the program may include instructions for performing some or all of operations of the processor 120.

The program may be pre-installed in the external device or may be downloaded and installed by a user of the external device from a server which provides applications. The server providing applications may include a record medium in which the program is stored.

The memory 150 may store data or programs for driving and controlling the ultrasound imaging apparatus 100, input/output ultrasonic data, ultrasonic images, etc.

The input interface 170 may receive a user input for controlling the ultrasound imaging apparatus 100. For example, the user input may include an input of operating a button, a keypad, a mouse, a trackball, a jog switch, a knop, etc., an input of touching a touch pad or a touch screen, a voice input, a motion input, or a biometrics input (e.g., iris recognition, fingerprint recognition, etc.); however, the disclosure is not limited thereto.

Figure 2A:
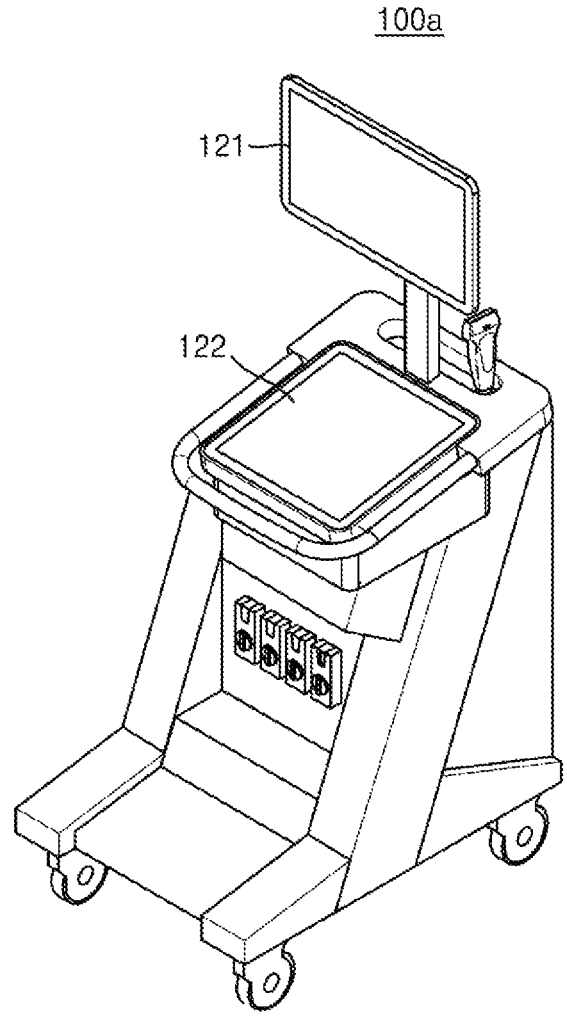
FIGS. 2A, 2B, and 2C are each a diagram of an ultrasound imaging apparatus according to an embodiment.
Figure 2B:
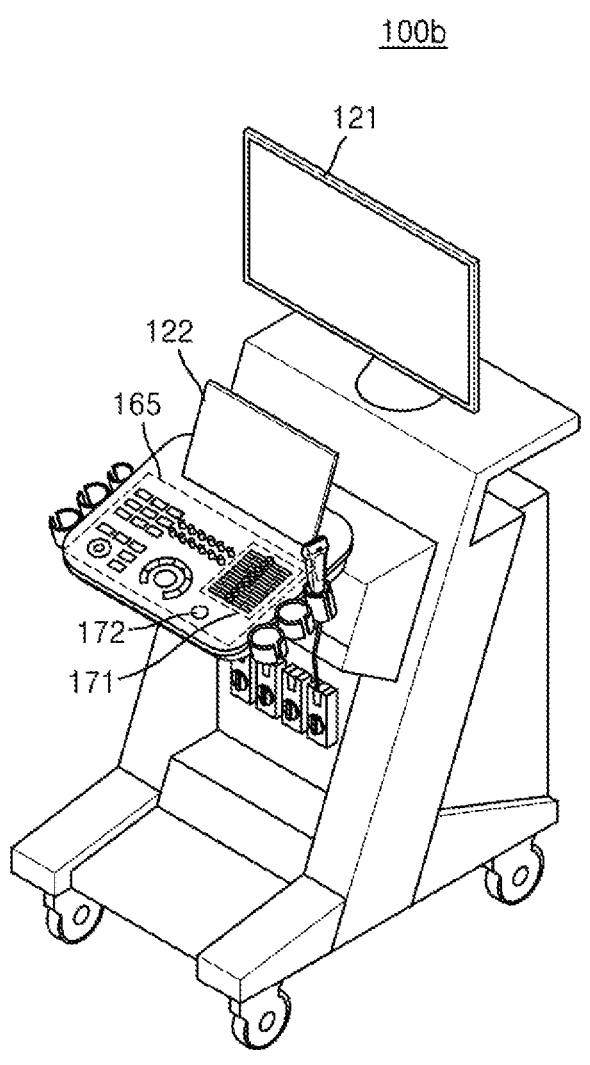
Figure 2C:
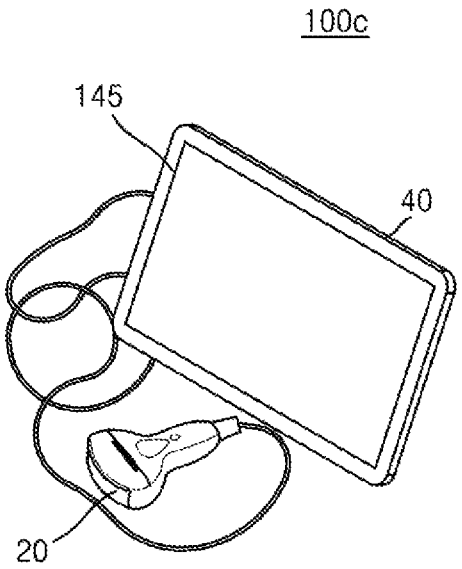

An example of the ultrasound imaging apparatus 100 according to an embodiment is further described in relation to FIGS. 2A, 2B, and 2C.

FIGS. 2A, 2B, and 2C are each a diagram of an ultrasound imaging apparatus according to an embodiment.

Referring to FIGS. 2A and 2B, an ultrasound imaging apparatus (100a or 100b) may include a main display 121 and a sub-display 122. One of the main display 121 and the sub-display 122 may be a touch screen. At least one of the main display 121 or the sub-display 122 may display an ultrasonic image or various information processed in the ultrasound imaging apparatus (100a and 100b). At least one of the main display 121 or the sub-display 122 may be a touch screen, and may receive from a user data input for controlling the ultrasound imaging apparatus (100a and 100b) by providing a graphical user interface (GUI). For example, the main display 121 may display an ultrasonic image, and the sub-display 122 may display a control panel for controlling the display of the ultrasonic image in the form of GUI. The sub-display 122 may receive data input for controlling the display of the image through the control panel displayed in the form of GUI. The ultrasound imaging apparatus (100a and 100b) may control the display of the ultrasonic image on the main display 121 by using the received control data.

Referring to FIG. 2B, the ultrasound imaging apparatus 100b may further include a control panel 165 in addition to the main display 121 and the sub-display 122. The control panel 165 may include a button, a trackball, a jog switch, a knop, etc., and may receive data for controlling the ultrasound imaging apparatus 100b from a user. For example, the control panel 165 may include a time gain compensation (TGC) button 171, a freeze button 172, etc. The TGC button 171 may be a button for setting a TGC value by a depth of an ultrasonic image. When an input through the freeze button 172 is sensed during scanning of an ultrasonic image, the ultrasound imaging apparatus 100b may maintain display of a frame image at that time point.

The button, trackball, jog switch, knop, etc. included in the control panel 165 may be provided as a GUI on the main display 121 or the sub-display 122.

Referring to FIG. 2C, an ultrasound imaging apparatus 100c may be implemented as a portable type. A portable type ultrasound imaging apparatus 100c may include a smartphone, a laptop computer, a PDA, a tablet PC, etc., which include a probe and an application; however, the disclosure is not limited thereto.

The ultrasound imaging apparatus 100c may include a probe 20 and a main body 40, and the probe 20 may be connected to a side of the main body 40 in a wired or wireless manner. The main body 40 may include a touch screen 145. The touch screen 145 may display an ultrasonic image, various information processed in the ultrasound imaging apparatus 100c, a GUI, etc.

Figure 3:
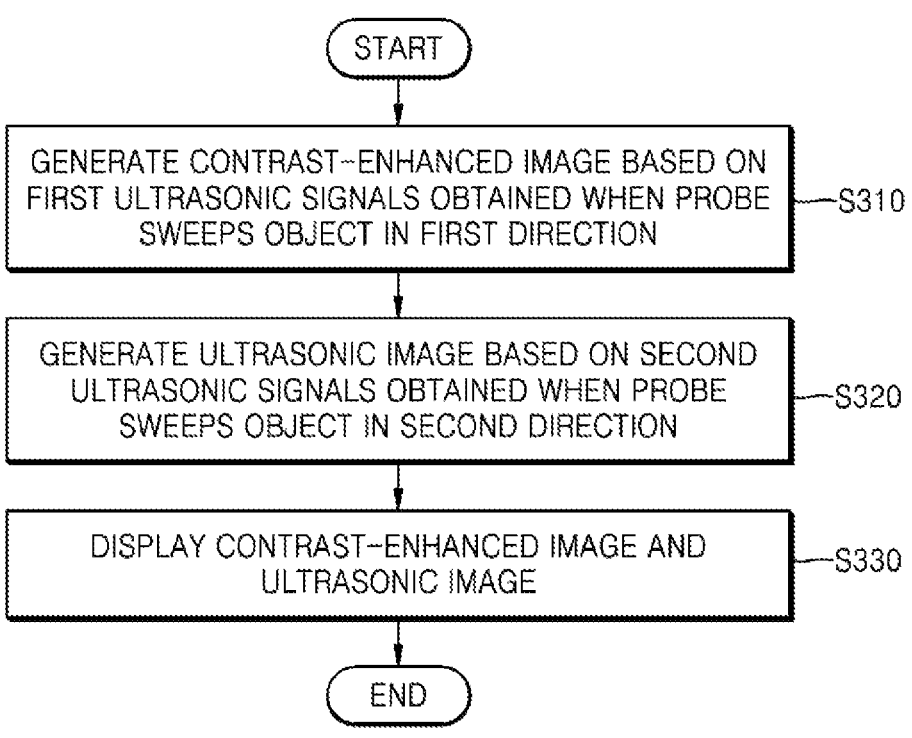
FIG. 3 is a flowchart illustrating a method of operating an ultrasound imaging apparatus according to an embodiment.

FIG. 3 is a flowchart illustrating a method of operating an ultrasound imaging apparatus according to an embodiment.

The ultrasound imaging apparatus 100 according to an embodiment may scan an object when the probe 20 sweeps the object. For example, the probe 20 may sweep the object in a first direction and a second direction opposite to the first direction. For example, when the probe 20 is a 1D probe in which a plurality of transducers are arranged in an azimuth direction, the probe 20 may sweep the object in an elevation direction by driving of a motor. The probe 20 may scan an object while rotating or moving by a certain distance in a first direction in which the elevation increases and may scan the object while rotating or sweeping by a certain distance in a second direction in which the elevation decreases. However, the disclosure is not limited thereto.

Alternatively, when the probe 20 is a 2D probe in which a plurality of transducers are arranged in an azimuth direction and an elevation direction, the probe 20 may sweep the object electrically. When the probe 20 is a 2D probe, the reciprocation in the first direction and the second direction may be unnecessary, and an object may be scanned when the probe 20 sweeps the object in one direction.

The ultrasound imaging apparatus 100 according to an embodiment may generate a contrast-enhanced image based on first ultrasonic signals obtained when the probe 20 sweeps the object in the first direction (S310).

The ultrasound imaging apparatus 100 may generate a contrast-enhanced image of the object 10 by irradiating an ultrasonic signal to the object 10 when the probe 20 sweeps the object in the first direction and receiving an echo signal for the irradiated ultrasonic signal.

For example, when the probe 20 sweeps the object in the first direction, the ultrasound imaging apparatus 100 may operate in a contrast-enhanced image mode.

A contrast-enhanced image may be an image showing various contrast patterns which appear when a microbubble ultrasonography contrast agent injected into the object 10 is spread to blood vessels and organ tissues of the object 10.

A contrast-enhanced image may be imaged by using the characteristics that echo signals reflected from microbubbles constituting an ultrasound contrast agent are shown as a strong signal compared to normal tissues. In the contrast-enhanced image mode, a transmission and reception method in which normal tissue signals are minimized and contrast-enhanced signals are emphasized in an image may be used to be differentiated from transmission and reception methods of tissue images.

Unlike human tissues, microbubbles have non-linear characteristics resonating at a particular frequency, and when an ultrasonic signal corresponding the resonant frequency, microbubbles may generate a relatively greater echo signal than tissues. In addition, as microbubbles are destroyed in a high-voltage environment of general tissue imaging, in a contrast-enhanced image mode, a signal having a lower voltage than a tissue image transmission signal may be used such that microbubbles are not destroyed in a human body.

An ultrasound imaging apparatus according to an embodiment may obtain a contrast-enhanced image by using a contrast-enhanced image transmission and reception method in the contrast-enhanced image mode.

For example, the contrast-enhanced transmission and reception method may include pulse inversion (PI), power modulation (PM), power modulated pulse inversion (PMPI), etc. The PI may be a transmission and reception method of obtaining a harmonic signal by irradiating two phase-inverted ultrasound transmission signals (waveform having a phase difference of) 180° to an object and summing echo signals reflected from the object. In a particular low-voltage section, echo signal reflected from tissues may cancel each other out, and a harmonic signal may not be generated. On the other hand, in a particular low-voltage section, echo signals reflected from a contrast agent may not cancel each other out, and a harmonic signal (contrast agent harmonic signal) may be generated. Such harmonic signal may include excellent resolution characteristics.

The PM may be a transmission and reception method of irradiating a plurality of ultrasound transmission signals of different amplitudes to an object, scaling echo signals reflected from the object by a transmission amplitude difference, and then obtaining a non-linear fundamental signal through subtraction. For example, the ultrasound imaging apparatus 100 may irradiate two consecutive ultrasound transmission signals, one of which has an amplitudes twice the amplitude of the other, to an object, double an echo signal by an ultrasound transmission signal of less amplitude (first ultrasound transmission signal), and carry out subtraction with respect to an ultrasound transmission signal of greater amplitude (second ultrasound transmission signal). In this regard, echo signals reflected from tissues in a particular low-voltage section may cancel each other out. On the other hand, as the amplitude of the echo signals by the second ultrasonic signals reflected from the contrast agent in a particular low-voltage section is more than twice the amplitude of the echo signals by the first ultrasonic signals, a signal component (contrast agent non-linear fundamental signal) may be generated. Such non-linear fundamental signal may have excellent medium penetration characteristics.

The ultrasound imaging apparatus 100 according to an embodiment may implement the PM by adjusting the amplitude of the ultrasound transmission signal using a transmission voltage. Alternatively, the ultrasound imaging apparatus 100 may implement the PM by controlling an effective transmitting aperture of the probe while maintaining the transmission voltage. By applying the same voltage to non-consecutive transducers among the plurality of transducers (e.g., even-numbered transducers or odd-numbered transducers), the ultrasound imaging apparatus 100 may have a halved effective transmitting aperture. In addition, as the same effect obtained by halving the applied voltage may be achieved, an error value due to voltage control may be minimized. However, the disclosure is not limited thereto.

The PMPI may be a method using both of PI and PM, in which ultrasound transmission signals having reversed phases and different amplitudes are irradiated to an object to simultaneously obtain a contrast agent non-linear fundamental signal and a harmonic signal. The ultrasound imaging apparatus 100 may obtain a contrast agent non-linear fundamental signal and a harmonic signal simultaneously based on an echo signal obtained by using a plurality of transducers, an echo signal obtained by using even-numbered transducers among the plurality of transducers, and an echo signal obtained by using odd-numbered transducers among the plurality of transducers. In this regard, an ultrasound transmission signal for a plurality of transducers and an ultrasound transmission signal for even/odd-numbered transducers may have a relation of reversed phase.

The ultrasound imaging apparatus 100 according to an embodiment may obtain a contrast-enhanced image by modulating a phase, an amplitude, etc. of an ultrasound transmission signal using the contrast-enhanced image transmission and reception methods described above. However, the contrast-enhanced image transmission and reception methods are not limited thereto.

As such, in the contrast-enhanced mode, it may be used a transmission and reception mode devised to emphasize a contrast-enhanced signal and effectively remove a tissue signal by applying an ultrasonic signal corresponding to a resonant frequency of microbubbles of a contrast agent under particular low-voltage conditions that do not destroy the microbubbles of the contrast agent. Ultrasonic images obtained in the contrast-enhanced image mode may be referred to as contrast-enhanced images. However, the disclosure is not limited thereto.

Specific low-voltage conditions used in the contrast-enhanced mode may vary according to a contrast agent. For example, the contrast agent may include SonoVue (Bracco SpA, Italy), Sonazoid (GE healthcare, USA), Definity (Lantheus Medical Imaging, USA), Optison (GE Healthcare, USA), etc. Specific low-voltage conditions for the above-listed ultrasound contrast agent may include voltage conditions corresponding to a mechanical index of 0.3 or less. However, the disclosure is not limited thereto.

The ultrasound imaging apparatus 100 according to an embodiment may generate an ultrasonic image based on second ultrasonic signals obtained when the probe 20 sweeps the object in the second direction (S320).

The ultrasound imaging apparatus 100 may generate an ultrasonic image of the object 10 by irradiating an ultrasonic signal to the object 10 when the probe 20 sweeps the object in the second direction and receiving an echo signal for the irradiated ultrasonic signal.

For example, when the probe 20 sweeps the object in the second direction, the ultrasound imaging apparatus 100 may operate in a B mode and obtain a tissue image.

For example, the ultrasound imaging apparatus 100 may obtain B mode data about an object and generate and display a B mode ultrasonic image (tissue image) based on the B mode data. The ultrasound imaging apparatus 100 may extract B mode components from the ultrasonic data and generate a B mode image in which intensity is expressed as luminance based on the extracted B mode components.

Or, the ultrasound imaging apparatus 100 may generate a Doppler (color Doppler or power Doppler) image, an elastography image, a microvascular image, etc. However, the disclosure is not limited thereto.

For example, the Doppler image may include an image showing the speed or intensity of blood flow in an object. For example, the ultrasound imaging apparatus 100 may irradiate a plurality of consecutive ultrasonic signals to an object and obtain signals reflected from moving blood flow. Based on the obtained reflected signals, the ultrasound imaging apparatus 100 may detect a frequency shift value due to the Doppler shift effect and obtain a speed or intensity of blood flow after removing a tissue signal using clutter filtering.

An elastography image may include an image showing a degree of modification of an object due to an ultrasonic signal irradiated to the object.

A microvascular image may include an image showing slow micro-blood flows included in an object. For example, the ultrasound imaging apparatus 100 may irradiate a plurality of consecutive ultrasonic signals to an object and obtain signals reflected from moving blood flow. Based on the reflected signals, the ultrasound imaging apparatus 100 may identify slow micro-blood flows through singular value decomposition (SVD).

The ultrasound imaging apparatus 100 according to an embodiment may display the contrast-enhanced image and the ultrasonic image respectively obtained in Operation 310 (S310) and Operation 320 (S320) on a display.

For example, the ultrasound imaging apparatus 100 may display the contrast-enhanced image and the ultrasonic image on one screen image. The ultrasound imaging apparatus 100 may display a 2D, 3D, or 4D contrast-enhanced image of an object in a first area. The ultrasound imaging apparatus 100 may display a 2D, 3D, or 4D tissue image (e.g., B mode image) of an object in a second area. Alternatively, the ultrasound imaging apparatus 100 may display a 2D, 3D, or 4D Doppler image, elastography image, microvascular image, etc. of an object in the second area. Size or ratio of the first area and the second area may be set or adjusted based on a user input.

The ultrasound imaging apparatus 100 may provide switching between contrast-enhanced image and the ultrasonic image on the display based on a user input. Alternatively, the ultrasound imaging apparatus 100 may overlay the contrast-enhanced image and the ultrasonic image on the display. However, the disclosure is not limited thereto.

Figure 4:
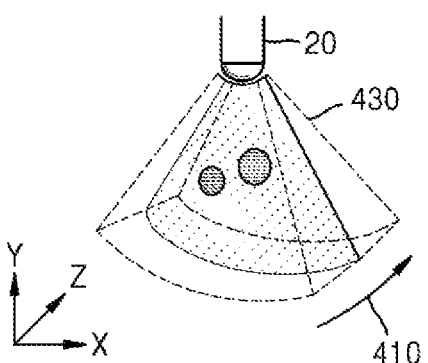
FIG. 4 is a diagram illustrating a method of obtaining a contrast-enhanced image and an ultrasonic image by an ultrasound imaging apparatus according to an embodiment.
Figure 4:
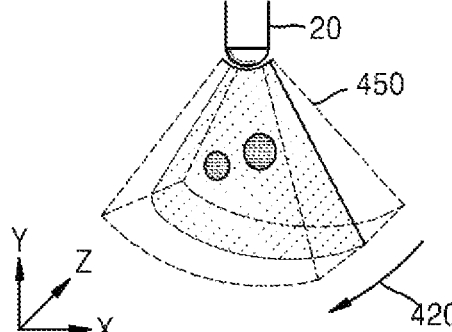

FIG. 4 is a diagram illustrating a method of obtaining a contrast-enhanced image and an ultrasonic image by an ultrasound imaging apparatus according to an embodiment.

Referring to FIG. 4, in the ultrasound imaging apparatus 100 according to an embodiment, an object may be scanned when the probe 20 sweeps the object in a first direction 410 and a second direction 420 opposite to the first direction 410.

Accordingly, the ultrasound imaging apparatus 100 according to an embodiment may obtain an ultrasound volume data of the object.

For example, when the probe 20 is a 1D probe in which a plurality of transducers included therein are arranged in an azimuth direction, the probe 20 may sweep the object in an elevation direction by driving of a motor. The probe 20 may transmit an ultrasonic signal to an object while rotating or moving in a forward direction in which the elevation increase and in a backward direction in which the elevation decreases and receive an echo signal reflected from the object.

When the probe 20 sweeps the object in the first direction 410 (e.g., forward direction), the ultrasound imaging apparatus 100 may operate in a contrast-enhanced mode. For example, the contrast-enhanced mode may use a transmission and reception mode devised to effectively emphasize a contrast-enhanced signal by applying an ultrasonic signal corresponding to a resonant frequency of microbubbles of a contrast agent under particular low-voltage conditions that do not destroy the microbubbles of the contrast agent. The ultrasound imaging apparatus 100 may generate a contrast-enhanced image in the contrast-enhanced mode.

A contrast-enhanced image may be an image generated by using the characteristics that echo signals reflected from microbubbles constituting an ultrasound contrast agent are shown as a strong signal compared to normal tissues.

When the probe 20 sweeps the object in the first direction 410, the ultrasound imaging apparatus 100 may obtain 2D contrast-enhanced images corresponding to a plurality of cross-sections of an object and generate a 3D contrast-enhanced image 430 (contrast-enhanced volume) based on the 2D contrast-enhanced images.

When the probe 20 sweeps the object in the second direction 420 (e.g., backward direction), the ultrasound imaging apparatus 100 may operate in the B mode. In the B mode, the ultrasound imaging apparatus 100 may generate a B mode ultrasonic image (tissue image).

Or, when the probe 20 sweeps the object in the second direction 420, the ultrasound imaging apparatus 100 may operate in a Doppler mode, a elastography mode, etc.

When the probe 20 sweeps the object in the second direction 420, the ultrasound imaging apparatus 100 may generate a B mode image (tissue image). In addition, the ultrasound imaging apparatus 100 may generate a color Doppler image, a power Doppler image, an elastography image, a microvascular image, etc.

The ultrasound imaging apparatus 100 according to an embodiment may adjust a resolution of a 3D tissue image 450 to be different from a resolution of the 3D contrast-enhanced image 430 by generating the 3D contrast-enhanced image 430 or the 3D tissue image 450 according to a sweeping direction.

For example, the ultrasound imaging apparatus 100 may set the number of 2D tissue images constituting the 3D tissue image 450 to be different from the number of 2D contrast-enhanced images constituting the 3D contrast-enhanced image 430. Moreover, the ultrasound imaging apparatus 100 may set the number of scanlines constituting one 2D tissue image to be different from the number of scanlines constituting one 2D contrast-enhanced image.

When the probe 20 repeatedly sweeps the object in the first direction 410 and the second direction 420, a 4D contrast-enhanced image and a 4D tissue image may be generated.

When the probe 20 rotates or moves in the first direction 410, the ultrasound imaging apparatus 100 may generate a first 3D contrast-enhanced image, and when the probe 20 rotates or moves in the second direction opposite to the first direction 410, the ultrasound imaging apparatus 100 may generate a first 3D tissue image. In addition, when the probe 20 rotates or moves again in the first direction 410, the ultrasound imaging apparatus 100 may generate a second 3D contrast-enhanced image, and when the probe 20 rotates or moves again in the second direction opposite to the first direction 410, the ultrasound imaging apparatus 100 may generate a second 3D tissue image. As such, when the probe 20 repeatedly sweeps the object in the first direction 410, the ultrasound imaging apparatus 100 may generate a plurality of 3D contrast-enhanced images. Based on the plurality of 3D contrast-enhanced images, the ultrasound imaging apparatus 100 may generate a 4D contrast-enhanced image.

When the probe 20 repeatedly sweeps the object in the second direction, the ultrasound imaging apparatus 100 may generate a plurality of 3D tissue images. Based on the plurality of 3D tissue images, the ultrasound imaging apparatus 100 may generate a 4D tissue image.

The ultrasound imaging apparatus 100 according to an embodiment may adjust the resolution of the 3D contrast-enhanced image 430 and the resolution of the 3D tissue image 450 to be different from each other and may adjust the volume rate of the 4D contrast-enhanced image and the 4D tissue image.

When the sweeping of the probe 20 is driven by a motor, a change in direction of the motor may cause a backlash phenomenon, and such backlash phenomenon may result in a difference between an ultrasonic image obtained in the forward direction and an ultrasonic image obtained in the backward direction, which leads to image shaking.

When the probe 20 sweeps the object in the first direction (forward direction), the ultrasound imaging apparatus 100 according to an embodiment may obtain only a contrast-enhanced image, and when the probe 20 sweeps the object in the second direction (backward direction), the ultrasound imaging apparatus 100 may obtain a tissue image to prevent image shaking.

Figure 5:
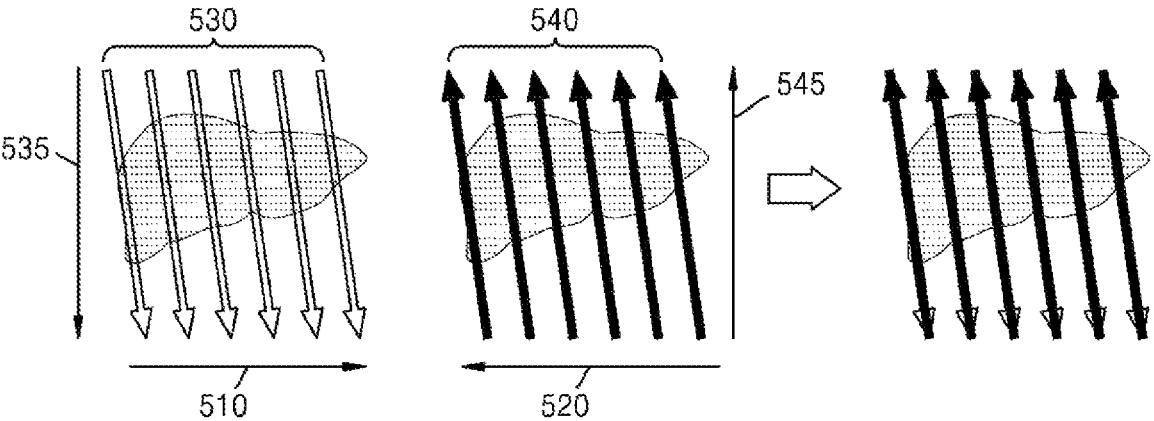
FIG. 5 is a diagram illustrating a method of generating a three-dimensional (3D) contrast-enhanced image and a 3D tissue image by an ultrasound imaging apparatus according to an embodiment.

FIG. 5 is a diagram illustrating a method of generating a 3D contrast-enhanced image and a 3D tissue image by an ultrasound imaging apparatus according to an embodiment.

Referring to FIG. 5, when the probe 20 sweeps the object in a first direction 510, the ultrasound imaging apparatus 100 according to an embodiment may obtain a plurality of 2D contrast-enhanced images corresponding to a plurality of cross-sections 530 of the object 10 based on the obtained first ultrasonic signals. FIG. 5 illustrates the object 10 and positions of the plurality of cross-sections 530 corresponding to the plurality of 2D contrast-enhanced image seen from a lens surface of the probe 20. When the probe 20 sweeps the object in the first direction, the ultrasound imaging apparatus 100 may perform scanning in a third direction 535. As the scanning is performed in the third direction 535 while the probe 20 sweeps the object in the first direction 510, the plurality of cross-sections 530 corresponding to the plurality of 2D contrast-enhanced images may be inclined in a sweeping direction.

Referring to FIG. 5, when the probe 20 sweeps the object in the second direction 520, the ultrasound imaging apparatus 100 according to an embodiment may obtain a plurality of 2D tissue images corresponding to a plurality of cross-sections 540 of the object 10 based on the obtained second ultrasonic signals. FIG. 5 illustrates the object 10 and the plurality of cross-sections 540 corresponding to the plurality of 2D tissue images seen from a lens surface of the probe 20.

When the probe 20 sweeps the object in the second direction 520, the ultrasound imaging apparatus 100 may perform scanning in a fourth direction 545. As the scanning is performed in the third direction 545 while the probe 20 sweeps the object in the second direction 520, the plurality of cross-sections 530 corresponding to the plurality of 2D tissue images may be inclined in a sweeping direction (second direction).

According to the ultrasound imaging apparatus 100, a scanning direction 535 at the time when the probe 20 sweeps the object in the first direction 510 may be opposite to a scanning direction 545 at the time when the probe 20 sweeps the object in the second direction 520. Accordingly, the positions of the first cross-sections 530 may be identical to the positions of the second cross-sections 540. As the positions of the first cross-sections 530 are identical to the positions of the second cross-sections 540, the ultrasound imaging apparatus 100 may generate a 3D contrast-enhanced image and a 3D tissue image which correspond to the same volume.

However, a transmission signal transmitted to an object in the tissue image mode (e.g., B mode) for generating a tissue image may destroy microbubbles of a contrast agent. Accordingly, when the positions of the first cross-sections are identical to the positions of the second cross-sections, microbubbles of the contrast agent at the second cross-sections may be destroyed when 2D tissue images corresponding to the second cross-sections are generated, and after this, the quality of a contrast-enhanced image generated at the first cross-sections having the same positions as the second cross-sections may decrease.

Figure 6:
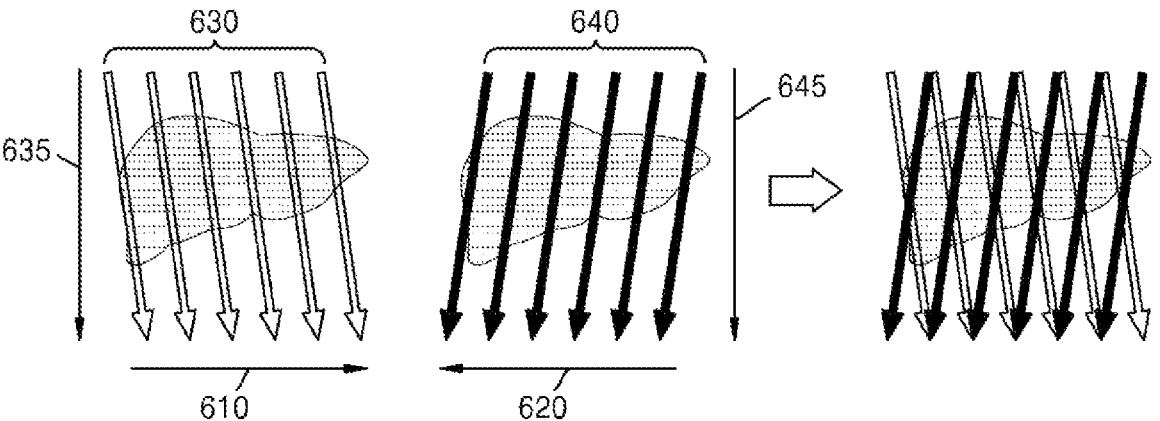
FIG. 6 is a diagram illustrating a method of generating a 3D contrast-enhanced image and a 3D tissue image by an ultrasound imaging apparatus according to an embodiment.

FIG. 6 is a diagram illustrating a method of generating a 3D contrast-enhanced image and a 3D tissue image by an ultrasound imaging apparatus according to an embodiment.

Referring to FIG. 6, when the probe 20 sweeps the object in a first direction 610, the ultrasound imaging apparatus 100 according to an embodiment may obtain a plurality of 2D contrast-enhanced images corresponding to a plurality of cross-sections 630 of the object 10 based on the obtained first ultrasonic signals. FIG. 6 illustrates the object 10 and positions of the plurality of cross-sections 630 corresponding to the plurality of 2D contrast-enhanced image seen from a lens surface of the probe 20. When the probe 20 sweeps the object in the first direction 610, the ultrasound imaging apparatus 100 may perform scanning in a third direction 635. As the scanning is performed in the third direction 635 while the probe 20 sweeps the object in the first direction 610, the plurality of cross-sections 630 corresponding to the plurality of 2D contrast-enhanced images may be inclined in a sweeping direction.

Referring to FIG. 6, when the probe 20 sweeps the object in a second direction 620, the ultrasound imaging apparatus 100 according to an embodiment may obtain a plurality of 2D tissue images corresponding to a plurality of cross-sections 640 of the object 10 based on the obtained second ultrasonic signals. FIG. 6 illustrates the object 10 and the plurality of cross-sections 640 corresponding to the plurality of 2D tissue images seen from a lens surface of the probe 20.

When the probe 20 sweeps the object in the second direction 620, the ultrasound imaging apparatus 100 may perform scanning in a fourth direction 645. As the scanning is performed in the fourth direction 645 while the probe 20 sweeps the object in the second direction 620, the plurality of cross-sections 640 corresponding to the plurality of 2D tissue images may be inclined in a sweeping direction (second direction).

According to the ultrasound imaging apparatus 100, a scanning direction 635 at the time when the probe 20 sweeps the object in the first direction 610 may be identical to a scanning direction 645 at the time when the probe 20 sweeps the object in the second direction 620. Accordingly, the positions of the first cross-sections 630 may be different from the positions of the second cross-sections 640.

Microbubbles of a contrast agent may be destroyed by an ultrasound transmission signals, and more specifically, the microbubbles may be destroyed more significantly by an ultrasound transmission signal transmitted in the tissue image mode than the contrast-enhanced image mode. A contrast-enhanced image may be an image generated based on an echo signal reflected from the microbubbles, and the quality of the contrast-enhanced image may deteriorate when the amplitude of the echo signal reflected from the microbubbles decreases due to destruction of the microbubbles.

Accordingly, the ultrasound imaging apparatus 100 according to an embodiment may increase duration of microbubbles of a contrast agent by avoiding transmission of a transmission signal for generating a contrast-enhanced image and a transmission signal for generating a tissue image to the same point.

As illustrated in FIG. 6, when the positions of the first cross-sections 630 corresponding to the contrast-enhanced image are different from the positions of the second cross-sections 640 corresponding to the tissue image, destruction of microbubbles of a contrast agent at the first cross-sections 630 may be reduced. Accordingly, deterioration of the quality of contrast-enhanced images corresponding to the first cross-sections 630 may be prevented.

Figure 7:
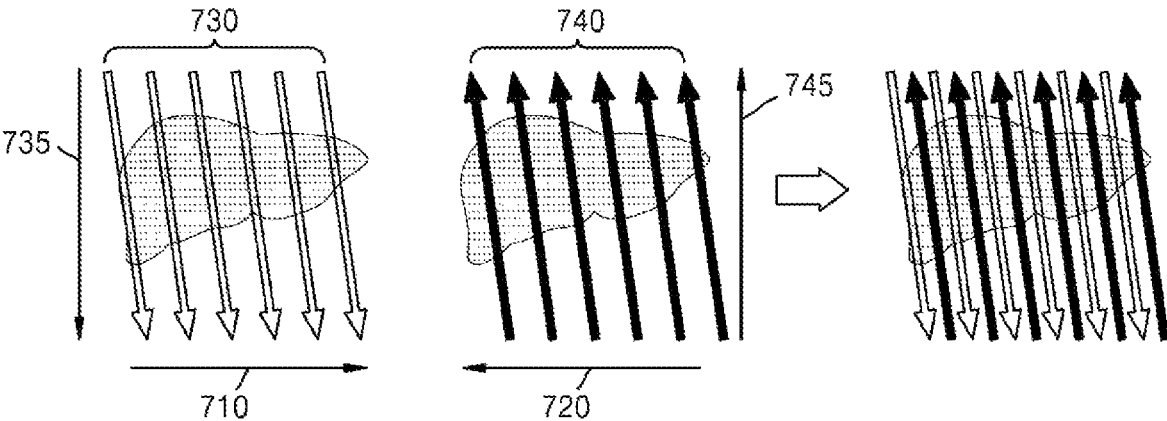
FIG. 7 is a diagram illustrating a method of generating a 3D contrast-enhanced image and a 3D tissue image by an ultrasound imaging apparatus according to an embodiment.

FIG. 7 is a diagram illustrating a method of generating a 3D contrast-enhanced image and a 3D tissue image by an ultrasound imaging apparatus according to an embodiment.

Referring to FIG. 7, when the probe 20 sweeps the object in a first direction 710, the ultrasound imaging apparatus 100 according to an embodiment may obtain a plurality of 2D contrast-enhanced images corresponding to a plurality of cross-sections 730 of the object 10 based on the obtained first ultrasonic signals. FIG. 7 illustrates the object 10 and positions of the plurality of cross-sections 730 corresponding to the plurality of 2D contrast-enhanced image seen from a lens surface of the probe 20. When the probe 20 sweeps the object in the first direction 710, the ultrasound imaging apparatus 100 may perform scanning in a third direction 735. As the scanning is performed in the third direction 735 while the probe 20 sweeps the object in the first direction 710, the plurality of cross-sections 730 corresponding to the plurality of 2D contrast-enhanced images may be inclined in a sweeping direction.

Referring to FIG. 7, when the probe 20 sweeps the object in a second direction 720, the ultrasound imaging apparatus 100 according to an embodiment may obtain a plurality of 2D tissue images corresponding to a plurality of cross-sections 740 of the object 10 based on the obtained second ultrasonic signals. FIG. 7 illustrates the object 10 and the plurality of cross-sections 740 corresponding to the plurality of 2D tissue images seen from a lens surface of the probe 20.

When the probe 20 sweeps the object in the second direction 720, the ultrasound imaging apparatus 100 may perform scanning in a fourth direction 745. As the scanning is performed in the fourth direction 745 while the probe 20 sweeps the object in the second direction 720, the plurality of cross-sections 740 corresponding to the plurality of 2D tissue images may be inclined in a sweeping direction (second direction).

According to the ultrasound imaging apparatus 100, a scanning direction 735 at the time when the probe 20 sweeps the object in the first direction 710 may be different from a scanning direction 745 at the time when the probe 20 sweeps the object in the second direction 720.

In addition, the ultrasound imaging apparatus 100 may control rotation or movement of the probe 20 such that the first cross-sections 730 and the second cross-sections 740 may not overlap and intersect each other. For example, the ultrasound imaging apparatus 100 may transmit an ultrasonic signal at an even-numbered angle such as 0°, 2°, 4°, etc. in the first direction 710 when the probe 20 sweeps the object in the first direction 710 and transmit an ultrasonic signal at an odd-numbered angle such as 1°, 3°, 5°, etc. when the probe 20 sweeps the object in the second direction 720. As such, the ultrasound imaging apparatus 100 may avoid transmission of a transmission signal for a contrast-enhanced image and a transmission signal for a tissue image to the same position. However, the disclosure is not limited thereto.

The ultrasound imaging apparatus 100 according to an embodiment may increase duration of microbubbles of a contrast agent and prevent deterioration of quality of contrast-enhanced images by avoiding transmission of a transmission signal for generating a contrast-enhanced image and a transmission signal for generating a tissue image to the same point.

FIGS. 5 to 7 illustrate that the ultrasound imaging apparatus 100 obtains a plurality of 2D contrast-enhanced images during the sweeping in the first direction and obtains a plurality of 2D tissue images during the sweeping in the second direction; however, the disclosure is not limited thereto.

For example, the ultrasound imaging apparatus 100 may obtain during the sweeping in the first direction a plurality of 2D contrast-enhanced images corresponding to a plurality of cross-sections of the object 10 based on the obtained first ultrasonic signals and obtain during the re-sweeping in the first direction a plurality of 2D tissue images corresponding to cross-sections of the object 10 based on the obtained second ultrasonic signals.

Or, the ultrasound imaging apparatus 100 may obtain during the sweeping in the second direction a plurality of 2D contrast-enhanced images corresponding to a plurality of cross-sections of the object 10 based on the obtained first ultrasonic signals and obtain during the re-sweeping in the second direction a plurality of 2D tissue images corresponding to cross-sections of the object 10 based on the obtained second ultrasonic signals.

Accordingly, the ultrasound imaging apparatus 100 may obtain a 3D contrast-enhanced image or a 3D tissue image through the sweeping in the first direction or in the second direction.

Moreover, the ultrasound imaging apparatus 100 may obtain a 4D contrast-enhanced image or a 4D tissue image by repeating the sweeping in the first direction or in the second direction and obtaining ultrasonic signals.

Figure 8:
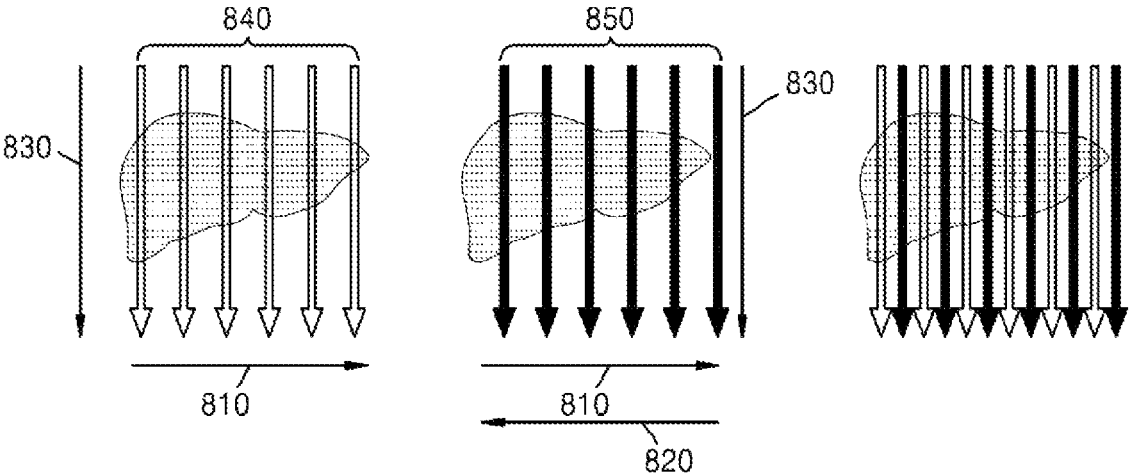
FIG. 8 is a diagram illustrating a method of generating a 3D contrast-enhanced image and a 3D tissue image by an ultrasound imaging apparatus according to an embodiment.

FIG. 8 is a diagram illustrating a method of generating a 3D contrast-enhanced image and a 3D tissue image by an ultrasound imaging apparatus according to an embodiment.

Referring to FIG. 8, when the probe 20 sweeps the object in a first direction 810, the ultrasound imaging apparatus 100 according to an embodiment may obtain a plurality of 2D contrast-enhanced images corresponding to a plurality of cross-sections 840 of the object 10 based on the obtained first ultrasonic signals. FIG. 8 illustrates the object 10 and positions of the plurality of cross-sections 840 corresponding to the plurality of 2D contrast-enhanced image seen from a lens surface of the probe 20. When the probe 20 first sweeps the object in the first direction 810, the ultrasound imaging apparatus 100 may perform scanning in a third direction 830. In this regard, the probe 20 may be a 2D probe in which a plurality of transducers are arranged in a 2D array. A 2D probe may scan an object by electrical sweeping instead of motor-driven sweeping. Thus, during the sweeping of the probe 20, the reciprocating motion between the first direction and the second direction may become unnecessary. In addition, as the sweeping is not motor-driven, the cross-sections 840 may not be inclined in a sweeping direction.

Accordingly, the ultrasound imaging apparatus 100 according to an embodiment may obtain second ultrasonic signals during a second sweeping of the probe 20 in the first direction 810 or in the second direction 820. The second sweeping may be performed in any direction; however, given the refusion time of microbubbles of contrast agent destroyed during the first sweeping, it may be effective to sweep the probe 20 in the first direction 810.

In addition, the ultrasound imaging apparatus 100 may perform scanning in the third direction 830 during the second sweeping of the probe 20 in the first direction 810 or in the second direction 820.

The ultrasound imaging apparatus 100 may obtain a plurality of 2D tissue images corresponding to a plurality of cross-sections 850 of the object 10 based on the second ultrasonic signals. FIG. 8 illustrates the object 10 and the plurality of cross-sections 850 corresponding to the plurality of 2D tissue images seen from a lens surface of the probe 20.

In addition, the ultrasound imaging apparatus 100 may control an ultrasonic signal transmission angle of the probe 20 such that the first cross-sections 840 and the second cross-sections 850 may be parallel with each other and intersect each other without overlapping. For example, the ultrasound imaging apparatus 100 may transmit an ultrasonic signal at an even-numbered angle such as 0°, 2°, 4°, etc. in the first direction 810 during the first sweeping of the probe 20 in the first direction 810 and transmit an ultrasonic signal at an odd-numbered angle such as 1°, 3°, 5°, etc. during the second sweeping of the probe 20 in the first direction 810 or in the second direction 820. As such, the ultrasound imaging apparatus 100 may avoid transmission of a transmission signal for a contrast-enhanced image and a transmission signal for a tissue image to the same position. However, the disclosure is not limited thereto.

The ultrasound imaging apparatus 100 according to an embodiment may increase duration of microbubbles of a contrast agent and prevent deterioration of quality of contrast-enhanced images by avoiding transmission of a transmission signal for generating a contrast-enhanced image and a transmission signal for generating a tissue image to the same point.

Figure 9:
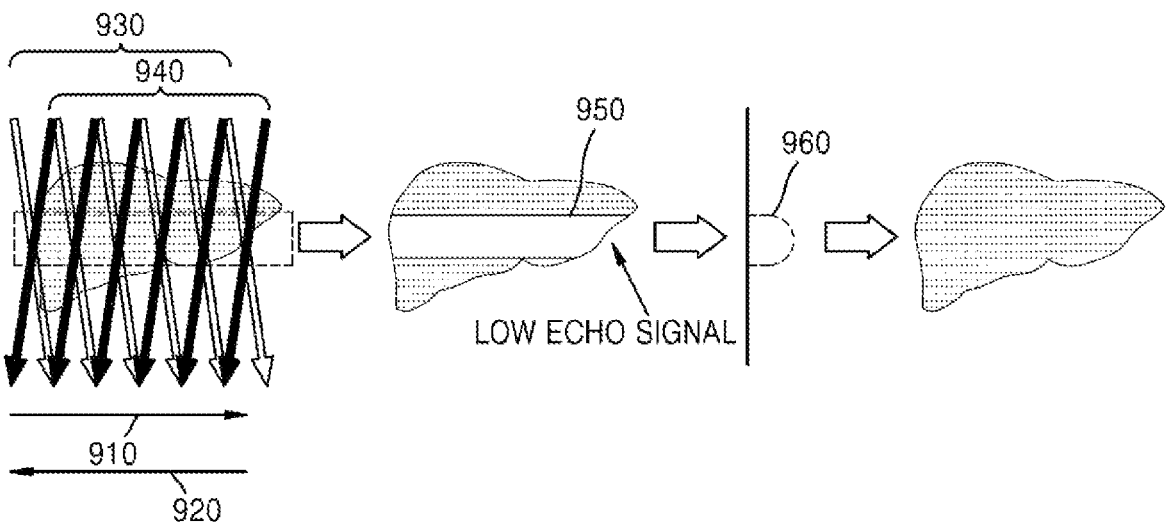
FIG. 9 is a diagram illustrating a method of generating a contrast-enhanced image by an ultrasound imaging apparatus according to an embodiment.

FIG. 9 is a diagram illustrating a method of generating a contrast-enhanced image by an ultrasound imaging apparatus according to an embodiment.

Referring to FIG. 9, when the probe 20 sweeps the object in a first direction 910, the ultrasound imaging apparatus 100 according to an embodiment may generate a plurality of 2D contrast-enhanced images corresponding to a plurality of first cross-sections 930 based on the obtained ultrasonic signals (contrast-enhanced signals).

In addition, when the probe 20 sweeps the object in the second direction, the ultrasound imaging apparatus 100 may generate a plurality of 2D tissue images corresponding to second cross-sections 940 based on the obtained ultrasonic signals (tissue signals).

In this regard, as a transmission signal for generating a contrast-enhanced image and a transmission signal for generating a tissue image are transmitted to an overlapping area 950 of the first cross-sections 930 and the second cross-sections 940, more microbubbles of a contrast agent may be destroyed, compared to other areas. Accordingly, an amplitude of an echo signal reflected from the overlapping area 950 of the first cross-sections 930 and the second cross-sections 940 may be less than that of echo signals reflected from other areas.

The ultrasound imaging apparatus 100 may apply a weighted value 960 to a gain set for the overlapping area 950 to compensate for the echo signal of the overlapping area 950. For example, a TGC value set for the overlapping area 950 may be adjusted by applying the weighted value 960 to the TGC value. The ultrasound imaging apparatus 100 may apply a gain to which the weighted value 960 is applied to a scanline signal of the overlapping area 950.

In addition, the ultrasound imaging apparatus 100 according to an embodiment may apply a weighted value to scanline gain compensation (SGC) set for the overlapping area 950 to adjust an SGC value. Gains may be set by scanline for SGC. Gain values may be applied in an analog or digital method.

For example, the ultrasound imaging apparatus 100 may apply a first gain value to the overlapping area 950 and apply a second gain value less than the first value to other areas.

Or, the ultrasound imaging apparatus 100 may apply a gain to which a weighted value is applied to the overlapping area 950 when generating a 2D contrast-enhanced image based on an echo signal received from an object. However, the disclosure is not limited thereto.

Figure 10:
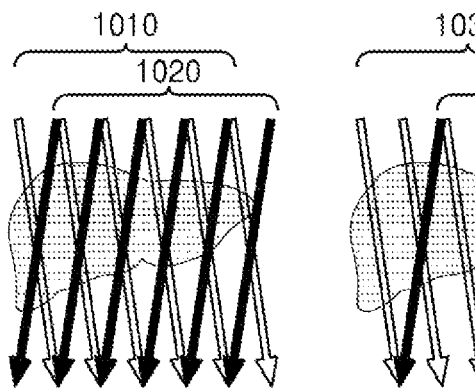
FIG. 10 is a diagram illustrating a method of generating a 3D contrast-enhanced image and a 3D tissue image by an ultrasound imaging apparatus according to an embodiment.
Figure 10:
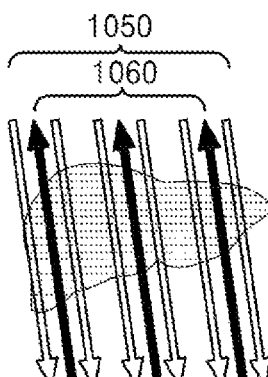

FIG. 10 is a diagram illustrating a method of generating a 3D contrast-enhanced image and a 3D tissue image by an ultrasound imaging apparatus according to an embodiment.

Referring to FIG. 10, the ultrasound imaging apparatus 100 according to an embodiment may adjust a resolution of a 3D contrast-enhanced image and a resolution of a tissue image to adjust a volume rate of a 4D contrast-enhanced image and a 4D tissue image. A volume rate may represent a rate of displaying volume data and may show the number of volume images (3D contrast-enhanced image or 3D tissue image) displayed per second. However, the disclosure is not limited thereto.

The ultrasound imaging apparatus 100 according to an embodiment may adjust each of a resolution of a 3D contrast-enhanced image and a resolution of a 3D tissue image.

For example, the ultrasound imaging apparatus 100 may adjust a resolution of a 3D contrast-enhanced image by adjusting quality of a transmission signal for generating a 3D contrast-enhanced image. The ultrasound imaging apparatus 100 may adjust the number of 2D contrast-enhanced images (frames) constituting a 3D contrast-enhanced image and the number of scanlines constituting a 2D contrast-enhanced image.

In addition, the ultrasound imaging apparatus 100 may adjust a resolution of a 3D tissue image by adjusting quality of a transmission signal for generating a 3D tissue image. The ultrasound imaging apparatus 100 may adjust the number of 2D tissue images (frames) constituting a 3D tissue image and the number of scanlines constituting a 2D tissue image.

As illustrated in FIG. 10, the ultrasound imaging apparatus 100 may set the number of 2D contrast-enhanced images constituting a 3D contrast-enhanced image to be 6 and the number of 2D tissue images constituting a 3D tissue image to be 6. Moreover, first cross-sections 1010 showing 2D contrast-enhanced images and second cross-sections 1020 showing 2D tissue images may be different from each other and may intersect each other.

The ultrasound imaging apparatus 100 may set the number of 2D contrast-enhanced images constituting a 3D contrast-enhanced image to be 6 and the number of 2D tissue images constituting a 3D tissue image to be 3. Moreover, third cross-sections 1030 showing 2D contrast-enhanced images and fourth cross-sections 1040 showing 2D tissue images may be different from each other and may intersect each other.

The ultrasound imaging apparatus 100 may set the number of 2D contrast-enhanced images constituting a 3D contrast-enhanced image to be 6 and the number of 2D tissue images constituting a 3D tissue image to be 3. Moreover, fifth cross-sections 1050 showing 2D contrast-enhanced images and sixth cross-sections 1050 showing 2D tissue images may be different from each other and may not intersect each other.

The ultrasound imaging apparatus 100 according to an embodiment may adjust the volume rate by adjusting the number of 2D contrast-enhanced images constituting a 3D contrast-enhanced image and the number of 2D tissue images constituting a 3D tissue image.

For example, the volume rate may increase more when the number of 2D contrast-enhanced images constituting a 3D contrast-enhanced image is set to 6, and the number of 2D tissue images constituting a 3D tissue image is set to 3 than when the number of 2D contrast-enhanced images constituting a 3D contrast-enhanced image is set to 6, and the number of 2D tissue images constituting a 3D tissue image is set to 6. When the volume rate increases, changes in contrast agent flow may be shown more clearly in a contrast-enhanced image.

Although FIG. 10 illustrates that the number of scanlines constituting a 2D contrast-enhanced image is the same as that of scanlines constituting a 2D tissue image, when the number of scan lines constituting a 2D tissue image decreases, the volume rate may increase.

The ultrasound imaging apparatus 100 according to an embodiment may increase a volume rate of a contrast-enhanced image while decreasing a resolution of a tissue image.

Figure 11:
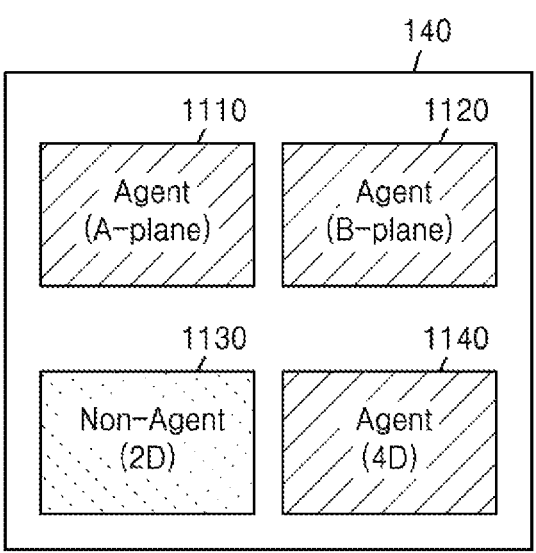
FIG. 11 is a diagram illustrating an example of a screen image showing a contrast-enhanced image and a tissue image displayed on a display by an ultrasound imaging apparatus.

FIG. 11 is a diagram illustrating an example of a screen image showing a contrast-enhanced image and a tissue image displayed on a display by an ultrasound imaging apparatus.

Referring to FIG. 11, the ultrasound imaging apparatus 100 according to an embodiment may display a contrast-enhanced image and a tissue image on one screen image. The screen image may include a plurality of areas. The ultrasound imaging apparatus 100 may display in each of the plurality of areas at least one of a 2D contrast-enhanced image, a 2D tissue image, a 3D contrast-enhanced image, a 3D tissue image, a 4D contrast-enhanced image, or a 4D tissue image.

For example, the screen image may be divided into four areas (1110, 1120, 11130, and 1140), and the ultrasound imaging apparatus 100 may display in the first area 1110 a 2D contrast-enhanced image showing a first cross-section of an object among a plurality of 2D contrast-enhanced images and display in the second area 1120 a 2D contrast-enhanced image showing a second cross-section of the object among a plurality of 2D contrast-enhanced images. The ultrasound imaging apparatus 100 may display in the third area 1130 a 2D tissue image showing a third cross-section of the object among a plurality of 2D tissue images. The ultrasound imaging apparatus 100 may display a 3D contrast-enhanced image or a 4D contrast-enhanced image in the fourth area 1140. However, the disclosure is not limited thereto, and the ultrasound imaging apparatus 100 may display various combinations of contrast-enhanced images and tissue images.

In addition, the ultrasound imaging apparatus 100 according to an embodiment may display, in addition to a tissue image, a Doppler image (color Doppler image or a power Doppler image), an elastography image, a microvascular image, etc. together with a contrast-enhanced image.

The ultrasound imaging apparatus 100 according to an embodiment may set a type of image to be displayed in each of the plurality of areas based on a user input. For example, the ultrasound imaging apparatus 100 may determine which image between a contrast-enhanced image and a tissue image is to be displayed and which image among a 2D image, a 3D image, and a 4D image is to be displayed, based on a user input.

The ultrasound imaging apparatus 100 may adjust a size or a ratio of each of the plurality of areas based on a user input.

Figure 12:
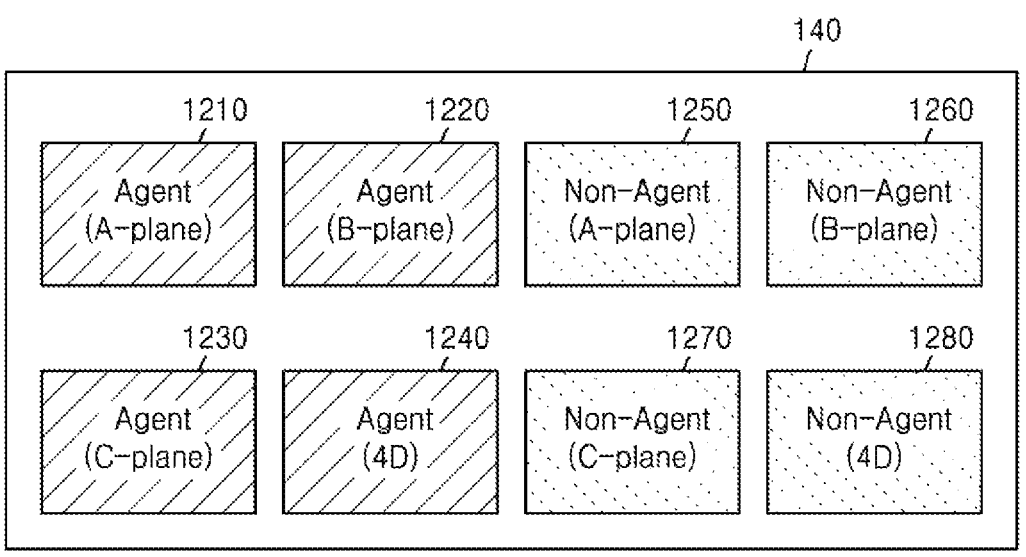
FIG. 12 is a diagram illustrating an example of a screen image showing a contrast-enhanced image and a tissue image displayed on a display by an ultrasound imaging apparatus.

FIG. 12 is a diagram illustrating an example of a screen image showing a contrast-enhanced image and a tissue image displayed on a display by an ultrasound imaging apparatus.

Referring to FIG. 12, the ultrasound imaging apparatus 100 according to an embodiment may divide the display screen into eight areas and display contrast-enhanced images in four areas (1210, 1220, 1230, and 1240) and non-contrast-enhanced images in the other four areas (1250, 1260, 1270, and 1280). The non-contrast-enhanced images may include a tissue image, a Doppler image, an elastography image, a microvascular image, etc.

The ultrasound imaging apparatus 100 may display 2D contrast-enhanced images showing different cross-sections of an object in the first to third areas 1210, 1220, and 1230. The different cross-sections of an object may be a sagittal plane, a transverse plane, and a coronal plane; however, the disclosure is not limited thereto.

The ultrasound imaging apparatus 100 may display a 4D contrast-enhanced image in the fourth area 1240.

The ultrasound imaging apparatus 100 may display 2D non-contrast-enhanced images showing different cross-sections of an object in the fifth to seventh areas 1250, 1260, and 1270. The different cross-sections of an object may be a sagittal plane, a transverse plane, and a coronal plane; however, the disclosure is not limited thereto.

The ultrasound imaging apparatus 100 may display a 4D non-contrast-enhanced image in the eighth area 1280.

The ultrasound imaging apparatus 100 may display non-contrast-enhanced images of different types in the fifth to eighth areas 1250, 1260, 1270, and 1280. For example, the ultrasound imaging apparatus 100 may display a 2D tissue image in the fifth and sixth areas 1250 and 1260, a 2D elastography image in the seventh area 1270, and a 4D color Doppler image in the eighth area 1280.

As a 3D contrast-enhanced image is generated based on an ultrasonic signal obtained when the probe 20 sweeps the object in the first direction, and a 3D non-contrast-enhanced image is generated based on an ultrasonic signal obtained when the probe 20 sweeps the object in the second direction, there may be a difference in time of image generation.

For example, when the probe 20 sequentially repeats sweeping in the first direction and sweeping in the second direction, a 3D contrast-enhanced image and a 3D non-contrast-enhanced image may be generated sequentially and repeatedly.

Accordingly, the ultrasound imaging apparatus 100 may display a 3D contrast-enhanced image generated first (first 3D contrast-enhanced image) and a 3D non-contrast-enhanced image generated first (first 3D non-contrast-enhanced image) together at a first time point. After the first time point, when a 3D contrast-enhanced image (second 3D contrast-enhanced image) is generated, the ultrasound imaging apparatus 100 may display the second 3D contrast-enhanced image and the first 3D non-contrast-enhanced image at a second time point. After the second time point, when a 3D non-contrast-enhanced image (second 3D non-contrast-enhanced image) is generated, the ultrasound imaging apparatus 100 may display the second 3D contrast-enhanced image and the second 3D non-contrast-enhanced image at a third time point. However, the disclosure is not limited thereto.

Figure 13:
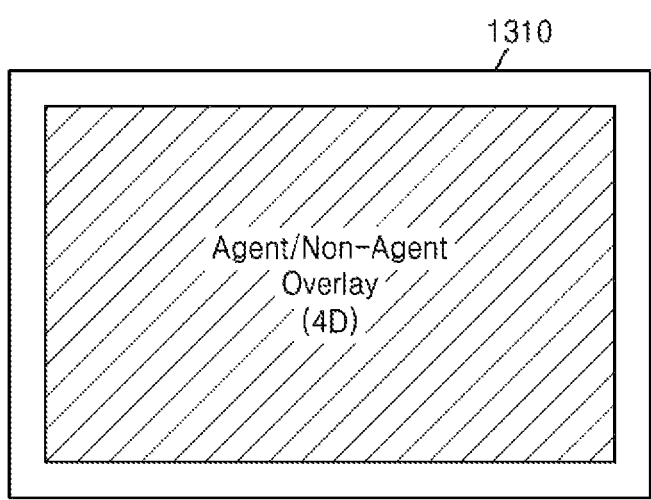
FIG. 13 is a diagram illustrating an example of a screen image showing a contrast-enhanced image and a tissue image displayed on a display by an ultrasound imaging apparatus.

FIG. 13 is a diagram illustrating an example of a screen image showing a contrast-enhanced image and a tissue image displayed on a display by an ultrasound imaging apparatus.

Referring to FIG. 13, the ultrasound imaging apparatus 100 according to an embodiment may display an overlay image of a contrast-enhanced image and a non-contrast-enhanced image on a display screen 1310. For example, the ultrasound imaging apparatus 100 may display an overlay image of a 3D contrast-enhanced image and a 3D non-contrast-enhanced image or display an overlay image of a 4D contrast-enhanced image and a 4D non-contrast-enhanced image.

When an overlay image of a 4D contrast-enhanced image and a 4D non-contrast-enhanced image is displayed, as described in relation to FIG. 12, an overlay image of a 3D contrast-enhanced image generated first (first 3D contrast-enhanced image) and a 3D non-contrast-enhanced image generated first (first 3D non-contrast-enhanced image) at a first time point may be displayed. After the first time point, when a 3D contrast-enhanced image (second 3D contrast-enhanced image) is generated, the ultrasound imaging apparatus 100 may display an overlay image of the second 3D contrast-enhanced image and the first 3D non-contrast-enhanced image at a second time point. After the second time point, when a 3D non-contrast-enhanced image (second 3D non-contrast-enhanced image) is generated, the ultrasound imaging apparatus 100 may display an overlay image of the second 3D contrast-enhanced image and the second 3D non-contrast-enhanced image at a third time point. However, the disclosure is not limited thereto.

The ultrasound imaging apparatus 100 according to an embodiment may facilitate identification of specific location of tissues in a contrast-enhanced image by displaying an overlay image of a contrast-enhanced image and a tissue image.

Figure 14:
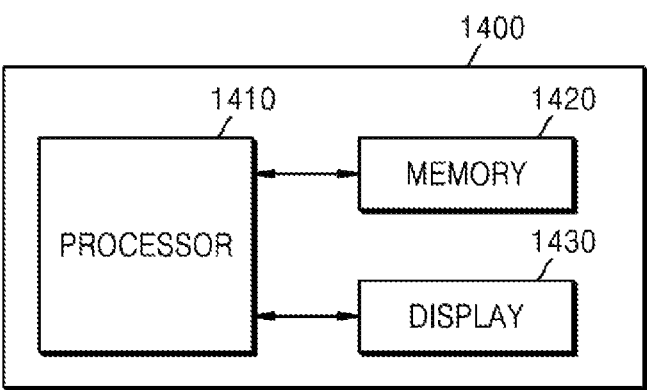
FIG. 14 is a block diagram illustrating components of an ultrasound diagnostic apparatus according to an embodiment.

FIG. 14 is a block diagram illustrating components of an ultrasound diagnostic apparatus according to an embodiment.

Referring to FIG. 14, an ultrasound imaging apparatus 1400 according to an embodiment may include a processor 1410, a memory 1420, and a display 1430.

The processor 1410 of FIG. 14 may correspond to at least one of the ultrasound transmission and reception module 110, the processor 120, or the image processor 130 or a combination thereof, and the display 1430 may correspond to the display 140 of FIG. 1. In addition, some of the components of the ultrasound imaging apparatus 100 illustrated in FIG. 1 according to an embodiment may be included in the ultrasound imaging apparatus 1400 illustrated in FIG. 14.

The processor 1410 according to an embodiment may control overall operations of the ultrasound imaging apparatus 1400. The processor 1410 according to an embodiment of the disclosure may execute one or more programs stored in the memory 1420.

The memory 1420 according to an embodiment of the disclosure may store data, programs, and applications for driving and controlling the ultrasound imaging apparatus 1400. The programs stored in the memory 1420 may include one or more instructions. The programs (one or more instructions) or applications stored in the memory 1420 may be executed by the processor 1410.

The processor 1410 according to an embodiment may generate a contrast-enhanced image based on first ultrasonic signals obtained when the probe sweeps the object in the first direction.

The processor 1410 may generate a contrast-enhanced image of the object by irradiating an ultrasonic signal to the object when the probe sweeps the object in the first direction and receiving an echo signal for the irradiated ultrasonic signal. For example, when the probe sweeps the object in the first direction, the processor 1410 may operate in a contrast-enhanced image mode. When operating in the contrast-enhanced mode, the processor 1410 may use a transmission and reception mode devised to emphasize a contrast-enhanced signal and effectively remove a tissue signal by applying an ultrasonic signal corresponding to a resonant frequency of microbubbles of a contrast agent under particular low-voltage conditions that do not destroy the microbubbles of the contrast agent. The processor 1410 may obtain a contrast-enhanced image in the contrast-enhanced mode.

The processor 1410 according to an embodiment may generate an ultrasonic image based on second ultrasonic signals obtained when the probe sweeps the object in the second direction. The processor 1410 may generate an ultrasonic image of the object by irradiating an ultrasonic signal to the object when the probe sweeps the object in the second direction and receiving an echo signal for the irradiated ultrasonic signal. For example, when the probe sweeps the object in the second direction, the processor 1410 may operate in the B mode and obtain a tissue image. The processor 1410 may obtain B mode data regarding the object, generate a B mode ultrasonic image (tissue image) based on the B mode data, and control the display 1430 to display thereon the generated image. The processor 1410 may extract B mode components from the ultrasonic data and generate a B mode image in which intensity is expressed as luminance based on the extracted B mode components. Or, the processor 1410 may generate a Doppler (color Doppler or power Doppler) image, an elastography image, a microvascular image, etc. However, the disclosure is not limited thereto.

The processor 1410 according to an embodiment may display a contrast-enhanced image and an ultrasonic image (non-contrast-enhanced image) on the display 1430. For example, the processor 1410 may control the display 1430 to display the contrast-enhanced image and the ultrasonic image on one screen image.

The display 1430 according to an embodiment may display an operational status of the ultrasound imaging apparatus 1400, an ultrasonic image, a user interface, etc.

The display 1430 may include one or more display panels according to an embodiment, and the display 1430 may be implemented in the form of a touch screen.

The processor 1410 may control the display 1430 to display a 2D, 3D, or 4D contrast-enhanced image of an object in a first area. The processor 1410 may control the display 1430 to display a 2D, 3D, or 4D tissue image (e.g., B mode image) of an object in a second area. Alternatively, the processor 1410 may control the display 1430 to display a 2D, 3D, or 4D Doppler image, elastography image, microvascular image, etc. of an object in the second area. Size or ratio of the first area and the second area may be set or adjusted based on a user input.

The processor 1410 may control the display 1430 to provide switching between a contrast-enhanced image and an ultrasonic image on a display based on a user input. The processor 1410 may control the display 1430 to display an overlay image of a contrast-enhanced image and an ultrasonic image. However, the disclosure is not limited thereto.

As an example of displaying a contrast-enhanced image and an ultrasonic image (non-contrast-enhanced image) on the display 1430 is already described in detail in relation to FIGS. 11 and 13, further description thereof is omitted.

The block diagram of the ultrasound diagnostic apparatus (100 and 1400) is for illustrating an embodiment. Components shown in the block diagram may be integrated, added, or omitted according to specifications of actually implemented ultrasound imaging apparatus (100 and 1400). That is, two or more components may be combined into a single component or a single component may be divided into two or more components, when necessary. Moreover, functions performed by each block are for illustrating embodiments, and specific operations and devices are not intended to limit the scope of rights of the disclosure.

A method of operating an ultrasound imaging apparatus according to an embodiment may be implemented in the form of a program command executable by various computer devices and recorded in a computer-readable medium. The computer-readable medium may include a program command, a data file, a data structure, etc. separately or combinedly. The program command recorded in the medium may be specifically designed and configured for the disclosure or may be made public and usable to a person skilled in the field of computer software. The computer-readable recording medium may include a hardware device specifically configured to store and execute program commands, such as magnetic media including a hard disk, a floppy disk, and a magnetic tape, optical media such as a CD-ROM and a DVD, magneto-optical media such as a floptical disk, ROM, RAM, flash memory, etc. The program commands may include not only machine language code, which is made by a compiler, but high level language code executable by a computer by using an interpreter, etc.

An ultrasound diagnostic apparatus and a method of operating an ultrasound diagnostic apparatus according to embodiments may be included and provided in a computer program product. A computer program product may be traded between a seller and a buyer.

A computer program product may include a S/W program and a computer-readable record medium in which the S/W program is stored. For example, a computer program product may include a product in the form of a S/W program electronically distributed by a manufacturer of electronic devices or an electronic market (e.g., Google Play Store, App Store, etc.) At least a part of the S/W program may be stored in a storage medium or temporarily generated for electronic distribution. In this case, a storage medium may be a storage medium of a manufacturer server, an electronic market server, or a relay server temporarily storing the S/W program.

The computer program product may include a storage medium of a server or a storage medium of a client device in a system consisting of a server and a client device. Alternatively, when there is a third device (e.g., smartphone) connected to a server or a client device, the computer program product may include a storage medium of the third device. Or, the computer program product may include a S/W program itself which is transmitted from a server to a client device or a third device or transmitted from a third device to a client device.

In this case, one of the server, client device, and third device may execute the computer program product and perform the method according to the embodiments. Or, two or more of the server, client device, and third device may execute the computer program product and perform the method according to the embodiments in a distributed manner.

For example, a server may control a client device connected to the server to perform the method according to the embodiments by executing the computer program product stored in the server (e.g., a cloud server or an artificial intelligence server).

An ultrasound imaging apparatus according to an embodiment may facilitate identification of specific location of tissues in a contrast-enhanced image by displaying a contrast-enhanced image and an ultrasonic image on one screen image.

An ultrasound imaging apparatus according to an embodiment may prevent image shaking due to the backlash phenomenon which may occur during a direction change of a motor which drives the probe for sweeping.

An ultrasound imaging apparatus according to an embodiment may minimize destruction of contrast agent by differentiating cross-sections of an object which correspond to contrast-enhanced images from cross-sections of the object which correspond to a tissue image.

An ultrasound imaging apparatus according to an embodiment may adjust a resolution of each of a contrast-enhanced image and a tissue image and may increase a volume rate.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. An ultrasound imaging apparatus comprising:
   a display;
   a memory storing one or more instructions; and
   a processor configured to execute the one or more instructions stored in the memory,
   wherein, by executing the one or more instructions, the processor is further configured to:
   generate at least one contrast-enhanced image corresponding to at least one first cross-section of an object based on first ultrasonic signals obtained when a probe sweeps the object in a first direction;
   generate at least one ultrasonic image corresponding to at least one second cross-section of the object based on second ultrasonic signals obtained when the probe sweeps the object in a second direction opposite to the first direction; and
control the display to display the at least one contrast-enhanced image and the at least one ultrasonic image,
wherein the processor is further configured to execute the one or more instructions to perform compensation for the first ultrasonic signals by applying a first gain value to the first ultrasonic signals obtained from a first area in which the at least one first cross-section and the at least one second cross-section intersect each other and applying a second gain value to the first ultrasonic signals obtained from areas other than the first area, and
wherein the first gain value is set to be greater than the second gain value.

2. The ultrasound imaging apparatus of claim 1, wherein the first ultrasonic signals include contrast-enhanced signals reflected from a contrast agent, and
the second ultrasonic signals include tissue signals reflected from tissues of the object.

3. The ultrasound imaging apparatus of claim 1, wherein the processor is further configured to execute the one or more instructions to:
generate, based on the first ultrasonic signals, contrast-enhanced images corresponding to first cross-sections of the object which do not intersect each other; and
generate, based on the second ultrasonic signals, ultrasonic images corresponding to second cross-sections of the object which do not intersect each other,
wherein the first cross-sections are different from the second cross-sections.

4. The ultrasound imaging apparatus of claim 3, wherein the first cross-sections and the second cross-sections do not intersect each other.

5. The ultrasound imaging apparatus of claim 3, wherein the processor is further configured to execute the one or more instructions to:
generate a three-dimensional (3D) contrast-enhanced image based on the contrast-enhanced images corresponding to the first cross-sections; and
generate a 3D ultrasonic image based on the ultrasonic images corresponding to the second cross-sections.

6. The ultrasound imaging apparatus of claim 5, wherein the 3D contrast-enhanced image has a first resolution, and the 3D ultrasonic image has a second resolution different from the first resolution.

7. The ultrasound imaging apparatus of claim 6, wherein the processor is further configured to execute the one or more instructions to set the number of the contrast-enhanced images constituting the 3D contrast-enhanced image to be different from the number of the ultrasonic images constituting the 3D ultrasonic image.

8. The ultrasound imaging apparatus of claim 6, wherein the first resolution is determined based on at least one of the number of the contrast-enhanced images constituting the 3D contrast-enhanced image or the number of scanlines constituting one contrast-enhanced image, and
the second resolution is determined based on at least one of the number of the ultrasonic images constituting the 3D ultrasonic image or the number of scanlines constituting one ultrasonic image.

9. The ultrasound imaging apparatus of claim 5, wherein a volume rate of the 3D contrast-enhanced image and the 3D ultrasonic image is determined based on the number of the contrast-enhanced images constituting the 3D contrast-enhanced image, the number of scanlines constituting one contrast-enhanced image, the number of the ultrasonic images constituting the 3D ultrasonic image, and the number of scanlines constituting one ultrasonic image.

10. The ultrasound imaging apparatus of claim 1, wherein the at least one ultrasonic image includes at least one of a tissue image, a Doppler image, an elastography image, or a microvascular image.

11. The ultrasound imaging apparatus of claim 1, wherein the processor is further configured to execute the one or more instructions to:

generate at least one second ultrasonic image of the object based on third ultrasonic signals obtained when the probe sweeps the object in a third direction different from the first direction and the second direction; and control the display to display the at least one second ultrasonic image.

12. A method of operating an ultrasound imaging apparatus, the method comprising:

generating at least one contrast-enhanced image corresponding to at least one first cross-section of an object based on first ultrasonic signals obtained when a probe sweeps the object in a first direction;

generating at least one ultrasonic image corresponding to at least one second cross-section of the object based on second ultrasonic signals obtained when the probe sweeps the object in a second direction opposite to the first direction; and displaying the at least one contrast-enhanced image and the at least one ultrasonic image, wherein the generating of the at least one contrast-enhanced image of the object includes performing compensation for the first ultrasonic signals by applying a first gain value to the first ultrasonic signals obtained from a first area in which the at least one first cross-section and the at least one second cross-section intersect each other and applying a second gain value to the first ultrasonic signals obtained from areas other than the first area, and wherein the first gain value is set to be greater than the second gain value.

13. The method of claim 12, wherein the first ultrasonic signals include contrast-enhanced signals reflected from a contrast agent, and the second ultrasonic signals include tissue signals reflected from tissues of the object.

14. The method of claim 12, wherein the generating of the at least one contrast-enhanced image of the object further includes generating, based on the first ultrasonic signals, contrast-enhanced images corresponding to first cross-sections of the object which do not intersect each other, and the generating of the at least one ultrasonic image of the object includes generating, based on the second ultrasonic signals, ultrasonic images corresponding to second cross-sections of the object which do not intersect each other, wherein the first cross-sections are different from the second cross-sections.

15. The method of claim 14, wherein the first cross-sections and the second cross-sections do not intersect each other.

16. The method of claim 14, wherein the generating of the at least one contrast-enhanced image of the object further includes generating a three-dimensional (3D) contrast-enhanced image based on the contrast-enhanced images corresponding to the first cross-sections, and the generating of the at least one ultrasonic image of the object includes generating a 3D ultrasonic image based on the ultrasonic images corresponding to the second cross-sections.

17. The method of claim 16, wherein the 3D contrast-enhanced image has a first resolution, and the 3D ultrasonic image has a second resolution different from the first resolution.

18. A non-transitory computer-readable recording medium having stored therein a program for executing the method of claim 12.

\* \* \* \* \*